United States Patent [19]

Mindich

[11] Patent Number: 4,793,346

[45] Date of Patent: Dec. 27, 1988

[54] PROCESS AND APPARATUS FOR HARVESTING VEIN

[76] Inventor: Bruce Mindich, 100 St. & 5th Ave., New York, N.Y. 10029

[21] Appl. No.: 904,047

[22] Filed: Sep. 4, 1986

[51] Int. Cl.$^4$ .............................................. A61B 17/32
[52] U.S. Cl. .................................. 128/305; 128/303.17
[58] Field of Search ............... 128/305, 303 R, 303.1, 128/303.13, 303.14, 303.17

[56] References Cited

U.S. PATENT DOCUMENTS

| | | | |
|---|---|---|---|
| Re. 29,088 | 12/1976 | Shaw | 128/303 |
| 1,867,624 | 7/1932 | Hoffman . | |
| 2,868,206 | 1/1959 | Stoesser | 128/303 R |
| 3,185,155 | 5/1965 | Slaten et al. | 128/303 R |
| 3,336,916 | 8/1967 | Edlich | 128/303.17 |
| 3,934,115 | 1/1976 | Peterson | 219/223 |
| 4,362,160 | 12/1982 | Hiltebrandt | 128/303 |
| 4,638,802 | 1/1987 | Okada | 128/303.17 |

FOREIGN PATENT DOCUMENTS

83/04174 12/1983 PCT Int'l Appl. .
510235 5/1976 U.S.S.R. .

*Primary Examiner*—C. Fred Rosenbaum
*Assistant Examiner*—Gene B. Kartchner
*Attorney, Agent, or Firm*—Bruce L. Adams; Van C. Wilks

[57] ABSTRACT

A section of a vein to be used for example in aorto-coronary bypass surgery, is harvested by making two incisions severing the vein at opposite ends of the section to be removed. A plastic guide is inserted in one incision, passed through the length of the vein section and out the other incision. A plastic tube having an inside diameter slightly larger than the outside diameter of the vein to be harvested and having two knife blades at its leading end is inserted into one of the incisions and slipped over the end of the vein section to be removed. The tube is pushed in over the vein section, while rotating the tube to sever vein branches by the knife blades and heating the knife blades electrically to cauterize ends of the severed branches, until the leading end of the tube reaches the other incision. The tube is then withdrawn with the vein section inside it.

19 Claims, 2 Drawing Sheets

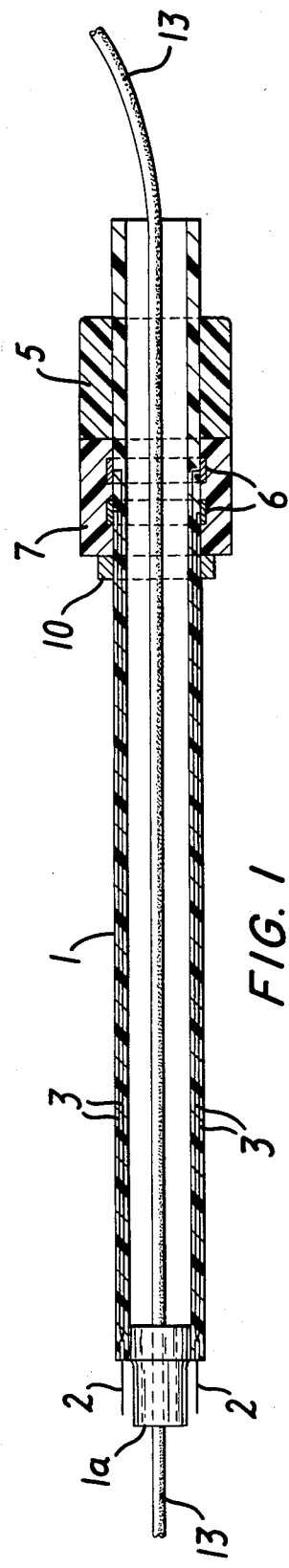
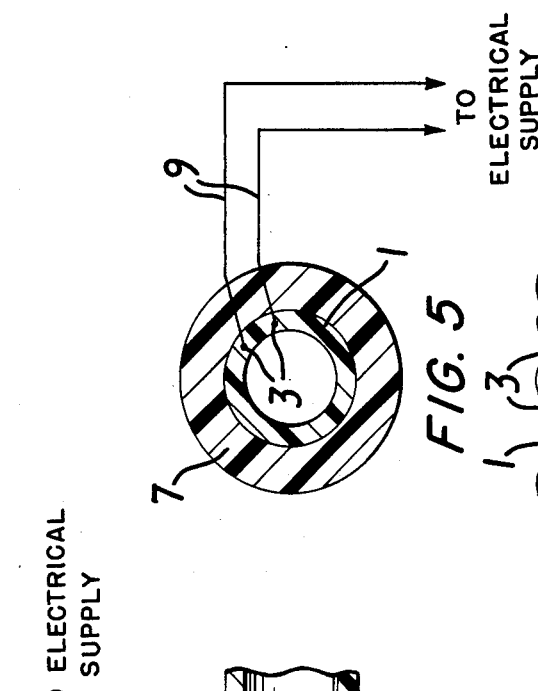
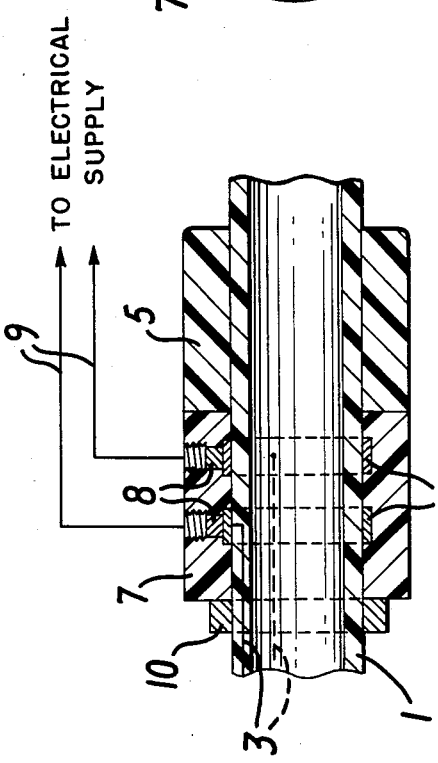
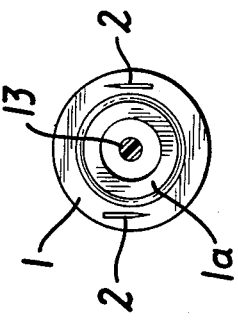

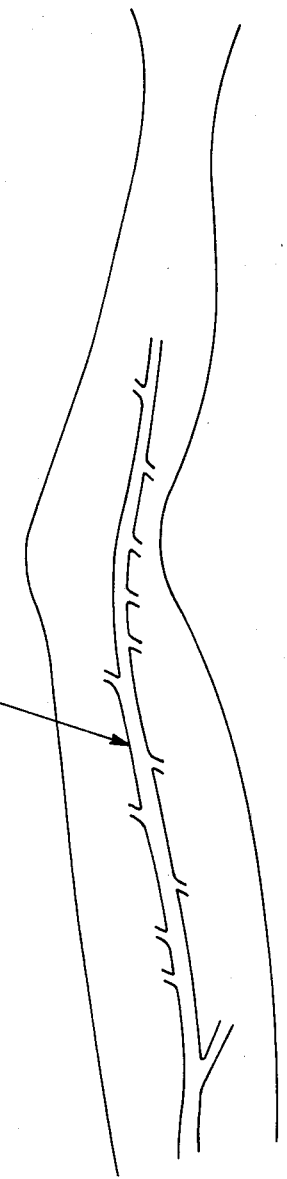
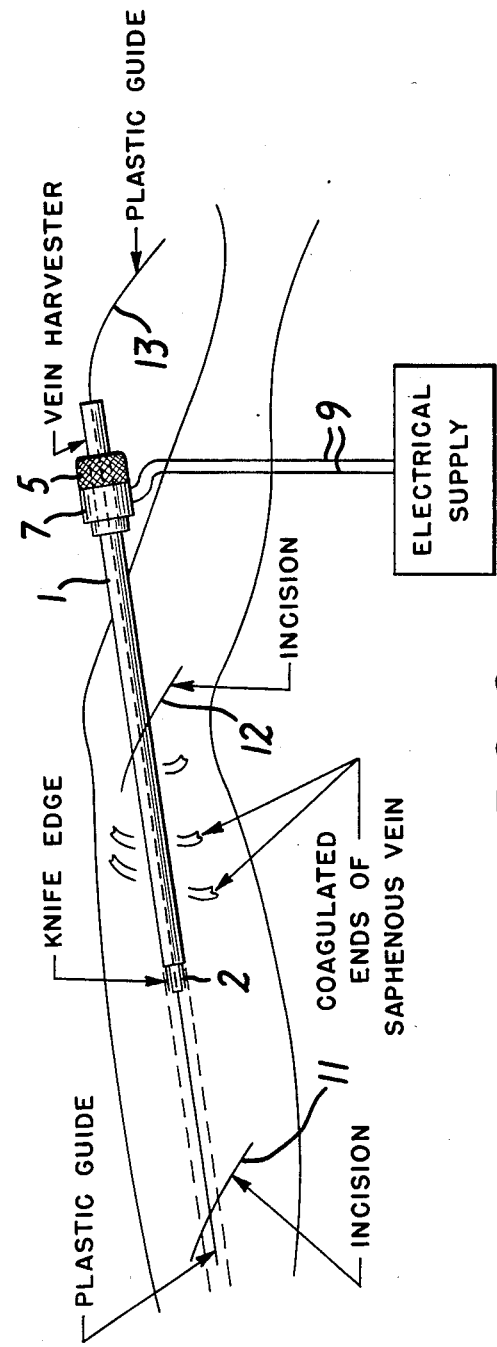
FIG. 8
FIG. 9

PROCESS AND APPARATUS FOR HARVESTING VEIN

FIELD OF INVENTION

The present invention relates to apparatus for harvesting veins and to the surgical procedure of using such apparatus.

BACKGROUND OF THE INVENTION

In certain surgical operations, it is necessary to remove a section of a vein from the patient. For example, a portion of the saphenous vein may be removed for use in aortocoronary bypass surgery. Heretofore, it has been necessary to make an incision along the vein of the full length of the section to be removed. The vein is then freed by severing the multiple branches branching off from the vein whereupon the vein section can be lifted out. The incision must then be closed, for example by suturing or staples.

SUMMARY OF THE INVENTION

It is an object of the invention to provide improved procedure in accordance with which a section of vein can be removed by making only small incisions at opposite ends of the vein section. The incisions are sufficiently deep as to expose the vein so that a vein section to be removed is severed from the remainder of the vein. A plastic tube having an inner diameter slightly larger than the outer diameter of the vein and having at least one knife blade at its leading end is inserted into one of the incisions and slipped over the respective end of the vein section to be removed. The tube is then pushed along the vein while rotating the tube so as to sever branches of the vein by the knife blade mounted at the leading end of the tube. Electrical current is supplied to the knife blade so as to heat it and thereby cauterize the ends of the severed branches. This procedure is continued until the leading end of the tube has reached the other of the two incisions. The tube is then withdrawn with the vein section inside it. The vein section can thereupon be removed from the tube and used as required.

BRIEF DESCRIPTION OF DRAWINGS

The nature, objects and advantages of the invention will be more fully understood from the following description in conjunction with the accompanying drawings in which:

FIG. 1 is a schematic longitudinal section of a surgical instrument in accordance with the invention comprising an elongate plastic tube having knife blades mounted at one end and a collar at the opposite end.

FIG. 2 is an enlarged schematic end view looking at the left hand end of the instrument as shown in FIG. 1.

FIG. 3 is an enlarged schematic view of one of the knife blades.

FIG. 4 is an enlarged schematic end view similar to FIG. 2 but showing curved knife blades.

FIG. 5 is an enlarged schematic end view looking at the right hand end of the instrument as shown in FIG. 1.

FIG. 6 is a schematic sectional view illustrating electrical connections.

FIG. 7 is an enlarged longitudinal section of a right hand end portion of the instrument shown in FIG. 7.

FIG. 8 is a schematic view showing the course of the saphenous vein, a section of which is to be removed.

FIG. 9 is a schematic view illustrating use of the surgical instrument in accordance with the present invention.

DESCRIPTION OF PREFERRED EMBODIMENT

As illustrated by way of example in the drawings, apparatus in accordance with the invention comprises an elongate plastic tube 1 having an inner diameter greater than the outer diameter of the vein section to be removed and having a length greater than the length of such section. For example, the tube may have a length of approximately 60 cm. It is formed for example by extrusion from a suitable, preferably clear, plastic and has sufficient strength to resist axial and torsional forces while being sufficiently flexible of permit at least slight bending. The tube, for example, may be formed of polyethylene or polypropylene.

At one end portion of the tube, herein referred to as the "leading" or "distal" end of the tube, two knife blades 2 are mounted opposite one another, for example by being set in slots in the end of the tube. One of the knife blades is shown enlarged in FIG. 3. It comprises a central portion 2a of electrically insulating material, for example ceramic or plastic, and a peripheral portion 2b formed of electrically conductive material preferably of relatively high electrical resistance. For example, the peripheral portion of the knife may be formed of stainless steel. One edge portion of the knife blade forms the cutting edge 2c. The knife blades can be flat as illustrated in FIG. 2 or they can be curved with approximately the same curvature as the tube wall as illustrated in FIG. 4. As will be described more fully below, the tube is slipped over a section of vein that is to be removed and is rotated so that branches of the vein are severed by the cutting edges of the knife blades as the tube is advanced. Thus the two knives are arranged with their cutting edges in the same rotational direction. While it is preferred to have two knife blades as illustrated, a single knife blade or more than two knife blades can be used if desired.

In order to avoid any danger of the knife blades cutting the vein that is being removed, the tube 1 is provided at its leading end with a guide or nose portion 1a which is of smaller diameter than the balance of the tube and extends between the knife blades. As illustrated in FIG. 1, the tips of the knife blades are set back a short distance, for example 3 mm, from the end of the guide portion 1a of the tube.

Electric current is supplied to heat the knife blades 2 so as to cauterize the vein branches as they are severed. For this purpose, electrical conductors, for example wires 3, extend length-wise of the plastic tube 1 and are connected with the knife blades by a coupling 4. As illustrated in FIG. 3, the conductive peripheral portion of each blade is U-shaped, one conductor being connected with one leg of the U and the other conductor being connected with the other leg. Current thus flows through the peripheral portion of the blade to heat it by resistance heating. The conductors 3 are embedded in the wall of the tube so that they do not in any way interfere with its rotation.

At the trailing or proximal end portion of the tube there is provided a collar 5 by means of which the tube is grasped and manipulated. The collar 5 is preferably also formed of plastic and the outer surface of the collar is preferably knurled or roughened so as to provide a non-slip grip. The collar 5 is suitably secured to the end portion of the tube, for example by a press-fit or welding.

In order to provide electric current to the conductors 3, the tube 1 is provided on its outer surface forwardly of the collar 5 with two slip rings 6 which are electrically connected respectively with the conductors 3. The slip rings 6 are surrounded by a second collar 7 which is rotatable on the tube 1 and is provided with resiliently pressed brushes 8 engaging the slip rings 6 respectively. The brushes 8 are connected to wires 9 leading to a suitable source of electrical energy for supplying electric current. The rotatable collar 7 is retained in position axially of the tube by a ring 10 affixed to the tube wall. It will be understood that as the tube 1 is rotated by the collar 5, the collar 7 remains rotationally stationary and hence the wires 9 are not twisted by rotation of the tube.

The procedure of removing a section of vein with the instrument illustrated in FIGS. 1-6, is illustrated schematically in FIGS. 8 and 9 of the drawing. FIG. 8 illustrates schematically the course of the saphenous vein in the leg. In removing a section of such vein according to the procedure of the present invention, two incisions 11 and 12 are made in the leg at locations representing the ends of the vein section to be removed. The incisions are preferably made at an angle to the course of the vein as illustrated in FIG. 9 and are sufficiently deep to sever the vein. Severed ends of the portions of the vein that are to remain are tied off or otherwise closed to avoid bleeding. A flexible plastic guide 13, which may be a monofilament or multifilament and is of greater length than the vein section to be removed, is inserted in one incision and passed entirely through the vein section to be removed and brought out of the other incision. The tube 1 is then manually grasped by the surgeon at the collar 5 and inserted over the trailing end of the flexible guide 13 and manually advanced forwardly along the guide while being turned or rotated to thereby sever the vein branches by means of the knife blades 2. Moreover, electric current is supplied to the knife blades through the slip rings 6 and conductors 3 so as to heat the knife blades to a temperature sufficiently high to cauterize the severed ends of the branches in order to inhibit bleeding. The collar 7 carrying the brushes 8 by which electric current is supplied to the slip rings 6 does not rotate. In other words, the tube 1 rotates in the non-rotating collar 7. The collar 7 may be held by the surgeon to assist in guiding the tube 1 while rotating it by means of the collar 5.

The advance of the tube 1 along the vein section is continued until the leading end of the tube reaches the other incision, for example the incision 11 as shown in FIG. 9. Calibrations are preferably provided on the length of the tube so as to indicate how far the tube is inserted. When the leading end of the tube has reached the opposite incision, the tube is withdrawn with the harvested vein section inside it and the incisions 11 and 12 are sutured or otherwise closed.

It will thus be seen that with the apparatus of the present invention, it is possible to remove a vein section by making only two small incisions at opposite ends of the section to be removed.

I claim:

1. Apparatus for harvesting a vein comprising: an elongate plastic tube having an inside diameter slightly larger than the outside diameter of a vein to be harvested, at least one knife blade mounted on the distal end of said tube in position to sever branches of the vein as said tube is slipped over the vein and is rotated as it is advanced, said tube having at its distal end a nose portion of reduced outside diameter extending radially inwardly of said knife blade and extending axially slightly beyond said knife blade, electrical conductors extending lengthwise of said tube and electrically connected to said knife blade to supply current to heat said knife blade and thereby cauterize the vein branches as they are severed, means at the proximal end of said tube for moving said tube axially over the vein and for rotating said tube as it is moved axially, and means for supplying electrical current to said conductors.

2. Apparatus according to claim 1, in which there are two of said knife blades disposed diametrically opposite one another on said tube.

3. Apparatus according to claim 1, in which said means for rotating said tube while moving it axially comprises a collar affixed on the proximal end of said tube.

4. Apparatus according to claim 3, in which said means for supplying electrical current to said conductors comprises slip rings on said tube electrically connected respectively to said conductors, an insulating collar rotatable on said tube around said slip rings and brush means carried by said rotatable collar and slidably engaging said slip rings respectively.

5. Apparatus according to claim 1, in which said knife blade comprises a central insulating portion and a peripheral electrically conductive cutting edge portion, said electrical conductors being electrically connected with said peripheral portion to pass current therethrough to heat said peripheral portion.

6. Apparatus according to claim 1, in which said tube is sufficiently flexible to follow a vein being harvested.

7. A process of harvesting a vein which comprises making a first incision at one end of a vein section to be harvested, making a second incision at the opposite end of said vein section, said incisions severing said vein, inserting into one of said incisions a plastic tube having an inside diameter slightly larger than the outside diameter of the vein to be harvested and having at least one knife blade on its leading end, slipping said tube over an end of said vein section and advancing said tube along said vein section while rotating said tube to sever branches of said vein section by said knife blade and passing electric current through said knife blade to heat said knife blade and thereby cauterize severed ends of said branches as said tube is advanced over said vein section, continuing the advance of said tube until said leading end reaches the other of said incisions and thereupon withdrawing said tube with said vein section inside it.

8. Process according to claim 7, in which a flexible plastic guide is inserted throughout the length of said vein section before said tube is advanced over said vein section, end portions of said guide extending out through said incisions.

9. A surgical instrument for harvesting a vein, comprising: an elongate tube having leading and trailing ends, an inside diameter larger than the outside diameter of a vein to be harvested, and being sufficiently flexible to follow the vein being harvested; severing means at the leading end portion of the tube for severing branches of the vein when the leading end of the tube is slipped over the vein and the tube is turned while being forwardly advanced lengthwise along the vein; means at the leading end of the tube for preventing accidental cutting of the vein by the severing means during forward advancement of the tube; manually graspable means at the trailing end portion of the tube for effecting manual advancement of the tube over and lengthwise along the vein and manual turning of the tube relative to the vein to thereby progressively gather the vein whose branches have been severed within the tube as the tube advances; and means carried by the tube for cauterizing branches of the vein severed by the severing means as the tube is forwardly advanced lengthwise along the vein.

10. A surgical instrument according to claim 9; wherein the means for preventing accidental cutting of the vein extends forwardly of the tube leading end a further distance than the severing means.

11. A surgical instrument according to claim 10; wherein the means for preventing accidental cutting of the vein comprises a tubular nose portion having an outside diameter smaller than that of the tube and extending forwardly of the leading end of the tube, the severing means being disposed radially outwardly of the nose portion.

12. A surgical instrument according to claim 11; wherein the severing means comprises at least one knife blade extending forwardly of the leading end of the tube.

13. A surgical instrument according to claim 12; wherein the means for cauterizing comprises an electrically conductive portion of the knife blade, and means connectable to a source of electrical energy during use of the surgical instrument for flowing electric current through the knife blade to thereby heat the knife blade to cauterize the severed vein branches.

14. A surgical instrument according to claim 13; wherein the means for flowing electric current comprises an electrically insulative collar turnably mounted on the tube, electrical conductors connected t one end to the knife blade and terminating at the other end at the collar, and means connected to the collar to undergo turning movement therewith for flowing electric current from the source of electrical energy to the electrical conductors.

15. A surgical instrument according to claim 14; wherein the electrical conductors are embedded within and extend lengthwise along the tube.

16. A surgical instrument according to claim 9; wherein the severing means comprises at least one knife blade extending forwardly of the leading end of the tube.

17. A surgical instrument according to claim 16; wherein the means for cauterizing comprises an electrically conductive portion of the knife blade, and means connectable to a source of electrical energy during use of the surgical instrument for flowing electric current through the knife blade to thereby heat the knife blade to cauterize the severed vein branches.

18. A surgical instrument according to claim 17; wherein the means for flowing electric current comprises an electrically insulative collar turnably mounted on the tube, electrical conductors connected at one end to the knife blade and terminating at the other end at the collar, and means connected to the collar to undergo turning movement therewith for flowing electric current from the source of electrical energy to the electrical conductors.

19. A surgical instrument according to claim 18; wherein in the electrical conductors are embedded within and extend lengthwise along the tube.

* * * * *